United States Patent [19]

Colley et al.

[11] Patent Number: 5,217,718
[45] Date of Patent: * Jun. 8, 1993

[54] METHOD AND DEVICE FOR ADMINISTERING DEXMEDETOMIDINE TRANSDERMALLY

[75] Inventors: Kenneth J. Colley; Donald R. Wilson, both of San Francisco; Gary W. Cleary, San Mateo, all of Calif.; Risto Lammintausta; Harry Jalonen, both of Turku, Finland

[73] Assignees: Cygnus Therapeutic Systems, Redwood City, Calif.; Farmos Group Ltd., Turku, Finland

[ * ] Notice: The portion of the term of this patent subsequent to Jun. 23, 2009 has been disclaimed.

[21] Appl. No.: 761,408

[22] Filed: Sep. 17, 1991

Related U.S. Application Data

[63] Continuation of Ser. No. 395,717, Aug. 18, 1989, Pat. No. 5,124,157.

[51] Int. Cl.$^5$ .............................................. A61F 13/00
[52] U.S. Cl. ...................................... 424/449; 424/448
[58] Field of Search ...................... 421/448, 449, 447

[56] References Cited

U.S. PATENT DOCUMENTS

| | | | |
|---|---|---|---|
| 3,598,122 | 8/1971 | Zaffaroni | 424/449 |
| 3,598,123 | 8/1971 | Zaffaroni | 424/449 |
| 3,926,188 | 12/1975 | Baker et al. | 424/449 |
| 5,124,157 | 6/1992 | Colley et al. | 424/449 |

Primary Examiner—Thurman K. Page
Attorney, Agent, or Firm—Morrison & Foerster

[57] ABSTRACT

Transdermal administration of dexmedetomidine, the dextrorotatory isomer of medetomidine, is described. The method involves sedating a patient by administering dexmedetomidine to a predetermined area of skin at an administration rate and for a time period effective to achieve the desired level of sedation. A therapeutic system for transdermally administering the drug is also provided. The therapeutic system is in the form of a skin patch which is a laminated composite of a backing layer, an optional anchor adhesive layer, a contact adhesive layer, and one or more additional layers.

28 Claims, 2 Drawing Sheets

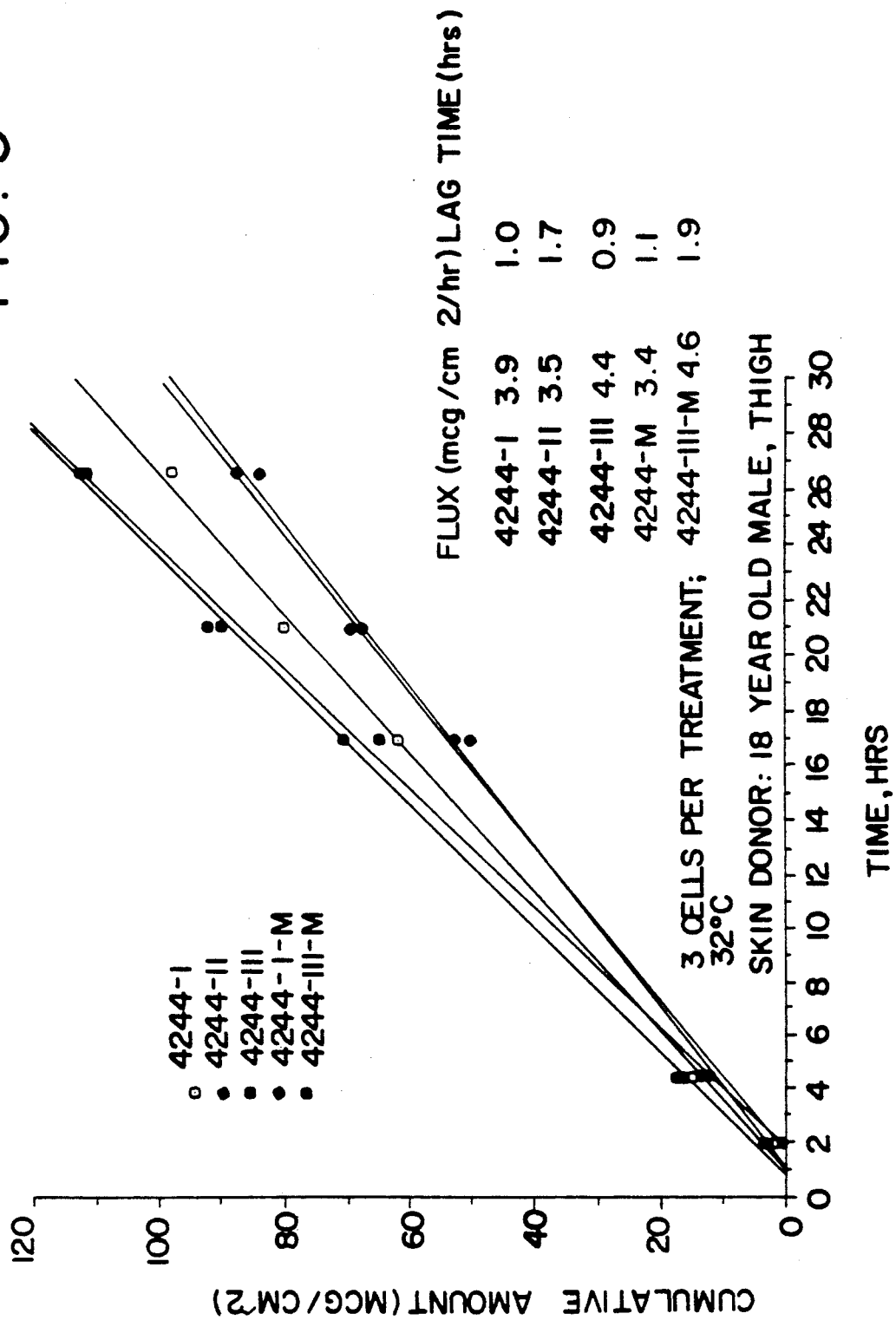

METHOD AND DEVICE FOR ADMINISTERING DEXMEDETOMIDINE TRANSDERMALLY

This application is a continuation of application Ser. No. 07/395,717 filed, 18 August 1989 now U.S. Pat. No. 5,124,157.

TECHNICAL FIELD

This invention relates generally to the administration of dexmedetomidine for sedative, hypotensive, analgesic and/or anxiolytic purposes, and more particularly relates to a method and device for administering the drug through the skin.

BACKGROUND

Medetomidine or 4(5)-[alpha-methyl-2,3-dimethylbenzyl] imidazole, having the structure

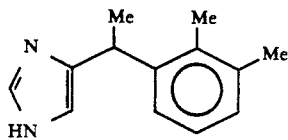

is a relatively new drug which is known to be a potent and selective alpha-2 receptor agonist. It has been identified to be useful as an antihypertensive agent (European Patent Publication No. 72615), a veterinary sedative (European Patent Publication No. 187471), and an anxiolytic (U.S. Pat. No. 4,783,477). Medetomidine, as may be inferred from its structure (I), comprises a mixture of optical isomers; the preparation, separation and purification of the dextrorotatory and levorotatory isomers has been described (see European Patent Publication No. 300652). It has also been established that the dextrorotatory isomer—"dexmedetomidine"—is the active isomer, while the 1-isomer is far less potent.

In addition to the above-cited art, the following references relate to the chemistry and pharmacology of medetomidine, its salts, and its component isomers: A. Karjalainen, *Acta Chem Scand* (1988) 42:537–545; E. MacDonald et al, *Eur J Pharmacol* (1988) 158:119–127; E. MacDonald et al, *Ann Clin Res* (1988) 20:298–310; R. Virtanen et al, *Eur J Pharmacol* (1988) 150:9–14; R. G. Vickery et al, *Anaesth Analg* (1988) 67:611–615; D. Stenberg et al, *J Vet Pharmacol Ther* (1987) 10:319–323; and M. Scheinin et al, *Br J Clin Pharmacol* (1987) 24:433451.

The present invention relates specifically to the administration of dexmedetomidine through the skin. Many systems have been developed and used to deliver drugs transdermally; the delivery of drugs through the skin has proved to have many advantages. Primarily, such a means of delivery is a comfortable, convenient and noninvasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug. Representative patents which describe transdermal drug delivery devices include U.S. Pat. Nos.: 3,598,122; 3,598,123; 3,731,683; 3,797,494; 3,854,480; 3,923,939; 3,926,188; 3,964,482; and 4,717,568.

None of the above-cited art or any other art of which applicants are aware describes a transdermal delivery device for administering dexmedetomidine. Nor does the prior art set forth data on skin permeability or therapeutic administration rates with respect to dexmedetomidine. To the best of applicants, knowledge, then, the transdermal administration of dexmedetomidine is unknown and completely unsuggested by the art.

SUMMARY OF THE INVENTION

Accordingly, it is a primary object of the invention to provide a method and device for administering dexmedetomidine transdermally.

It is another object of the invention to provide a method for sedating a patient, which comprises administering dexmedetomidine to the patient through a predetermined area of intact skin for a time period and at an administration rate sufficient to effect sedation.

It is still another object of the invention to provide a method for administering dexmedetomidine transdermally which involves coadministration with a skin permeation enhancer.

It is still a further object of the invention to provide a transdermal system for administering dexmedetomidine which comprises a laminated composite of a backing layer, an upper, optional anchor adhesive layer, a lower, contact adhesive layer which initially contains the drug, and a highly porous, structural intermediate layer between the two adhesive layers.

Further and other objects of the invention will be set forth in the description which follows, and in part will become apparent to those skilled in the art upon examination of the following, or may be learned by practice of the invention.

In one aspect, the invention is a method for sedating a patient by administering dexmedetomidine transdermally, i.e., administering the drug to the patient through a predetermined area of intact skin, the method premised on the discovery that dexmedetomidine may indeed be administered through the skin to achieve desired systemic effects. In a preferred embodiment, a skin permeation enhancer is coadministered with the drug so as to increase the permeability of the skin thereto and achieve more rapid delivery. As the clearance rate of dexmedetomidine from the body is quite high, it is preferred that administration be continuous throughout the period during which sedation is desired.

It should be noted that while the present invention is directed to the effect of dexmedetomidine as a sedative, "sedation" as used herein is intended to encompass all of the potential uses of the drug which derive from its activity as an alpha-2 receptor agonist, e.g., its use as a hypotensive agent, an anxiolytic, an analgesic, and the like.

In another aspect of the invention, a therapeutic system for administering dexmedetomidine transdermally is provided in the form of a skin patch. The skin patch is a laminated composite containing an upper backing layer and two distinct adhesive layers, the lower, "contact" adhesive layer initially formulated so as to contain the drug. It is also preferred that the laminated composite contain a highly porous intermediate layer between the two adhesive layers, e.g., of a nonwoven fabric or the like. This intermediate layer is completely permeable through the pores to the drug and to any vehicles or solubilizers contained within the device, and serves primarily as a structurally reinforcing layer, but not as a rate-controlling layer.

BRIEF DESCRIPTION OF THE DRAWINGS

FIG. 3 illustrates graphically the results of the experiment described in Example 2.

DETAILED DESCRIPTION OF THE INVENTION

Figure 1:
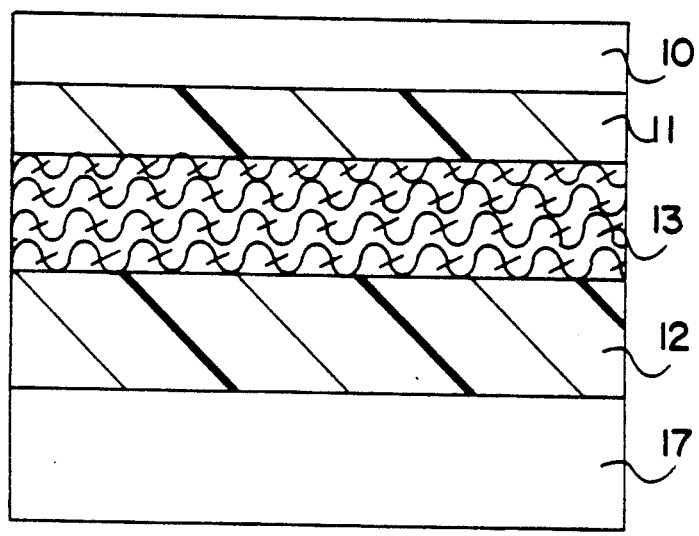
FIG. 1 depicts a cross section of a device of the invention immediately after lamination of the component layers.

The invention is thus a direct result of applicants's discovery that dexmedetomidine can be administered through the skin to achieve the drug's desired systemic effects, without any of the side effects or complications that frequently arise from oral or other types of systemic administration. The method of the invention involves transdermally administering dexmedetomidine for the purpose of "sedating" a patient, i.e., for use as an actual sedative, or for use as an antihypertensive, analgesic, anxiolytic, or the like. These various indications, as noted above, all derive from the fact that dexmedetomidine acts to effect alpha-adrenergic stimulation.

The method involves administering dexmedetomidine to a predetermined area of intact skin for a time period and at an administration rate effective to induce sedation. As the clearance rate of dexmedetomidine from the body is relatively high, it is preferred that administration of the drug be continuous throughout the time period during which sedation is desired. In order to achieve effective blood levels of the drug for light sedation, a preferred administration rate is between about 0.10 to about 200 ug/hr, more preferably in the range of about 15 to about 75 ug/hr, through a skin area of about 2.0 to about 90 cm$^2$, more preferably about 10 to about 30 cm$^2$. The amount of drug delivered into the skin may be controlled by a number of factors, including skin patch size, degree of initial drug loading, the use of a skin permeation enhancer, the use of different materials for the drug delivery device, and the like.

In some instances, it may be desirable to induce a rapid, high plasma concentration of dexmedetomidine. This may be effected by employing a second, rapidly-depleted transdermal device in addition to the zero-order release device of the invention. This supplemental device delivers a large initial amount of dexmedetomidine to establish an effective concentration in the subject, and thereafter decays exponentially to zero over a period of 0.5-2 hours. Thus, the net effect is a high initial concentration, which gradually declines to the steady-state administration of the zero-order deliver device of the invention. The supplemental device is preferably applied to highly permeable skin, such as the forehead. Such a system is particularly useful for surgical anesthesia, in which the supplemental device in combination with the zero-order device provide enough dexmedetomidine to anesthetize the patient, followed by a period of lower, postoperative sedation effected by the zero-order device alone.

The preferred chemical form of dexmedetomidine for transdermal administration is the free base, as the skin is somewhat more permeable to the base form of the drug than its salts. The acid addition salts of the drug may, however, be administered transdermally if desired, provided that a solubilizing vehicle is used as well as, preferably, a skin permeation enhancer. Such acid addition salts may be formed, for example, with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

While not essential for transdermal administration of the drug, it is preferred that a skin permeation enhancer be coadministered therewith, whether the drug is administered in base or salt form. Any number of the many skin permeation enhancers known in the art may be used. Examples of suitable enhancers include dimethylsulfoxide (DMSO), dimethyl formamide (DMF), N,N-dimethylacetamide (DMA), decylmethylsulfoxide (C$_{10}$MSO), polyethylene glycol monolaurate (PEGML), glycerol monolaurate, ethanol, eucalyptol, lecithin, the 1-n-dodecylcyclazacycloheptan-2-ones (available under the trademark Azone® from Nelson Research & Development Co., Irvine, Calif.), and propylene glycol monolaurate (PGML).

Especially preferred skin permeation enhancers for use in conjunction with the transdermal administration of dexmedetomidine are esters given by the formula [CH$_3$(CH$_2$)$_m$COO]$_n$R, in which m is an integer in the range of 8 to 16, n is 1 or 2, and R is a lower alkyl (C$_1$-C$_3$) residue that is either unsubstituted or substituted with one or two hydroxyl groups. In the preferred embodiment herein, the ester component is a lower alkyl (C$_1$-C$_3$) laurate (i.e., m is 10 and n is 1), and in a particularly preferred case is "PGML". It will be appreciated by those skilled in the art that the commercially available material sold as "PGML" is typically a mixture of propylene glycol monolaurate itself, propylene glycol dilaurate, and either propylene glycol, methyl laurate, or both. Thus, the terms "PGML" or "propylene glycol monolaurate" as used herein are intended to encompass both the pure compound as well as the mixture that is typically obtained commercially. An "effective" amount of a skin permeation enhancer as used herein means an amount that will provide the desired increase in skin permeability and, correspondingly, the desired depth of penetration, rate of administration, and amount of drug delivered.

In general, carriers or vehicles will typically be present in the dexmedetomidine formulation along with a skin permeation enhancer. Since dexmedetomidine base is a solid, a solubilizer of some sort is necessary to administer the drug transdermally. A selected skin permeation enhancer may serve this purpose; alternatively, one or more solubilizers may be present in addition to a skin permeation enhancer. Other carriers or vehicles may be present as well: these terms include carrier materials that are generally suitable for transdermal drug administration, and which are nontoxic and do not interact with other components of the composition in a deleterious manner. Examples of suitable carriers and vehicles for use herein include water, mineral oil, silicone, liquid sugars, waxes, petroleum jelly, and other oils and polymeric materials.

Figure 2:
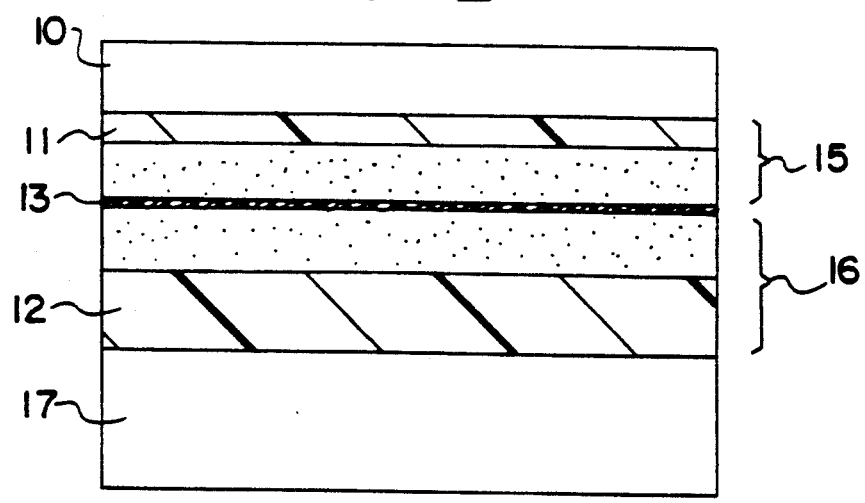
FIG. 2 depicts a cross section of the device shown in FIG. 1, after the layers have had time to interpenetrate.

The therapeutic system for transdermally administering dexmedetomidine according to the method of the invention is a laminated composite as shown in FIGS. 1 and 2. The device (1) comprises: (a) a backing layer (10) which serves as the upper surface of the device; (b) an optional anchor adhesive layer (11) adjacent the backing layer; and (c) a contact adhesive layer (12) which defines the basal surface of the device and which contacts and adheres to the skin during use. The composite also preferably contains (d) an optional porous intermediate layer (13) between the anchor and contact adhesive layer where an anchor layer is included, typically of an adsorbent, nonwoven fabric. After lamination, the anchor adhesive and contact adhesive soak into the intermediate layer to form a composite layer (14) having an upper portion (15) comprising intermediate layer and anchor adhesive, and a lower portion (16) comprising intermediate layer and contact adhesive. When packaged, prior to administration, the device will also preferably comprise a release liner (17), laminated to the exposed contact layer surface.

The backing layer functions as the primary structural element of the device and provides the device with much of its flexibility, suitable drape, and where necessary, occlusivity. The backing layer may also serve as a protective covering to prevent loss of drug and/or vehicle via transmission through the upper surface of the device. The backing layer may be used to impart a degree of occlusivity to the device, such that the area of skin covered on application becomes hydrated. The backing is preferably made of a sheet or film of a preferably flexible elastomeric material that is substantially impermeable to dexmedetomidine. The layer is preferably on the order of 0.0005" to about 0.003" in thickness, and may optionally be pigmented, metalized, or provided with a matte finish suitable for writing. The layer is preferably of a material that permits the device to follow the contours of the skin, and be worn comfortably on areas of skin such as at joints or other points of flexure, that are normally subjected to mechanical strain with little or no likelihood of the device disengaging from the skin due to differences in the flexibility or resiliency of the skin and the device. Examples of elastomeric polymers useful for the backing layer are polyether amide block polymers such as PEBAX polymers, polyethylene methyl methacrylate block polymers (EMA) such as NUKRELL polymers, polyurethanes such as PELLATHANE or ESTANE polymers, silicone elastomers, polyester block polymers composed of hard and soft segments (e.g., HYTREL polymers), rubber-based polyisobutylene, styrene, and styrene-butadiene and styrene-isoprene copolymers. Flexible polymers include polyethylene, polypropylene, polyesters, (e.g., polyester terephthalate, "PET"), and the like, which may be provided as films or laminates. The particular polymer used for the backing will depend on the material incorporated into the device, including the vehicle, solubilizer, permeation enhancer, etc. The presently preferred flexible backing material is a 1 mil matte finished polyester film suitable for writing, obtainable from DuPont (Mylar) and ICI Americas Inc. (Melinex). Another presently preferred material is a metalized polyester laminated with polyethylene, available from 3M as #1109. An alternatively preferred backing material is a transparent polyester (3M #139).

The optional anchor layer adheres to the backing layer and to the contact layer. The anchor layer is particularly preferred in embodiments of the device which employ permeation enhancers, as the enhancer will otherwise tend to promote separation of the backing and contact adhesive layers. The anchor adhesive must be compatible with dexmedetomidine and the vehicle employed. It is preferred that dexmedetomidine have low solubility in the anchor layer, and especially that it not partition significantly into the anchor layer from the contact layer. Accordingly, the particular adhesive selected for the anchor layer will depend in part upon the contact layer composition and backing materials selected, and in part on the relative partition coefficients between the contact and anchor layers. Suitable adhesives for the anchor layer include polysiloxanes, polyisobutylenes, polyacrylates, polyurethanes, plasticized ethylene-vinyl acetate copolymers, low molecular weight polyether amide block polymers (e.g., PEBAX), tacky rubbers such as polyisobutene, polystyrene-isoprene copolymers, polystyrene-butadiene copolymers, and mixtures thereof. Presently preferred anchor adhesives are polyisobutylenes, acrylates, and silicones, particularly polyisobutylenes. The anchor layer will generally be about 10 to about 75 um in thickness, preferably about 50 um (about 2 mil). It will usually be thinner than the contact adhesive layer: this helps to minimize the amount of drug partitioned into the anchor layer.

The contact adhesive is a pressure-sensitive adhesive suitable for long-term skin contact. It must also be physically and chemically compatible with dexmedetomidine and the carriers and vehicles employed. Further, the drug must be somewhat soluble in the adhesive, so that the drug does not partition into the anchor layer (away from the skin), but will partition into the skin. The material should also have a high diffusivity for dexmedetomidine. The contact layer will generally range in thickness from about 10 to about 100 um, preferably about 75 um. Suitable adhesives include polysiloxanes, polyisobutylenes, polyacrylates, polyurethanes, plasticized ethylene-vinyl acetate copolymers, low molecular weight polyether amide block polymers (e.g., PEBAX), tacky rubbers such as polyisobutene, polystyrene-isoprene copolymers, polystyrene-butadiene copolymers, and mixtures thereof. Presently preferred contact adhesives are acrylates, silicones, and polyurethanes.

The intermediate layer is a thin, flexible adsorbent layer which serves to immobilize both the anchor layer and the contact layer, preventing curling, delamination and cold flow of the assembled device. It is preferred, but not absolutely necessary, to include an intermediate layer. The intermediate layer is included only in those devices also containing an anchor layer. During fabrication of the device, the anchor adhesive and the contact adhesive migrate into the intermediate layer, meeting therein. The intermediate layer should be completely permeable to all components of the device, and thus does not function as a rate-controlling membrane. The layer is preferably fabricated from a nonwoven fabric such as polyester, polyethylene, polypropylene, polyamides, rayon, or cotton, especially 100% nonwoven polyester. Woven fabrics may alternatively be employed, but are less preferred. The intermediate layer is generally about 0.001" to about 0.010" in thickness.

The release liner is a disposable element which serves only to protect the device prior to application. Typically, the release liner is formed from a material impermeable to the drug, vehicle, and adhesives, and which is easily stripped from the contact adhesive. Release liners are typically treated with silicone or fluorocarbons. Silicone-coated polyester is presently preferred.

In general, devices of the invention are fabricated using methods standard in the art, by solvent evaporation film casting, thin film lamination, and die cutting. A presently preferred embodiment of the invention is prepared as follows:

A solution of two vinyl acetate-acrylate multipolymers in ethyl acetate, toluene (or alternatively isopropanol), and ethanol are prepared by weighing each polymer/solvent solution into a suitable vessel and mixing until smooth and homogeneous to form the contact layer solution. If desired, one may substitute an aqueous emulsion-based acrylate adhesive for the solvent based solution. The desired quantity of dexmedetomidine is added and thoroughly mixed. An enhancer (for example, PGML) is optionally added at this point. Next, a solution of polyisobutylene and polybutene polymers in hexane is prepared by weighing the polymers and hexane into a suitable vessel, and mixing until smooth and homogeneous, forming the anchor layer casting solution The anchor adhesive solution is then applied to the release-treated side of a release liner by, for example, extrusion die, coating knife, or knife-over-roll coating techniques. The hexane solvent is removed by passing the coating through a drying oven. Next, the backing layer is laminated to the dried anchor adhesive under uniform roll pressure The release liner is then stripped off, and a nonwoven fiber film laminated in its place under uniform roll pressure. The resulting laminate is wound onto a roll.

The drug/contact adhesive solution is then coated onto the release liner, and the solvents removed by passing the layer through a drying oven. The dried contact layer is then laminated to the fiber surface of the backing/anchor/fiber laminate under uniform roll pressure, allowing the anchor and contact adhesives to flow into the intermediate fiber layer. Finally, the laminate is diecut into individual devices, inspected, and heat-sealed into pouches.

EXAMPLES

The examples presented below are provided as a further guide to the practitioner of ordinary skill in the art, and are not to be construed as limiting the invention in any way.

EXAMPLE 1

Fabrication

An exemplary device of the invention was prepared as follows:

The contact adhesive layer was prepared by combining vinyl acetate-acrylate multipolymers (18.84% Gelva 737, and 75.36% Gelva 788) with propylene glycol monolaurate (PGML, 4.96%, obtained from Gattefosse) and dexmedetomidine (0.84%, free base, obtained from Farmos), and mixing in a stainless steel jar mill for 24 hrs, until smooth and homogeneous.

The resulting solution was cast onto a 3 mil siliconized polyester release liner (PolySlik ®, HP Smith). The casting solution was precisely deposited at 10 mils (pre-drying thickness) using a Gardner hand coating knife. The solvents were then removed by drying the cast film in a drying oven at 65° C. for 20 min.

The anchor adhesive layer was prepared by mixing two polybutene/polyisobutylenes (4.50% Vistanex L-100 PIB, and 22.50% Vistanex LM-MS-SC PIB, obtained from Exxon) with a polybutene tackifier (9.00% Indopol H1900 PB, obtained from Amoco) and hexane (64%). The combination was mixed for about 60 hrs, until smooth and homogeneous.

The resulting solution was cast onto a 3 mil siliconized polyester release liner (PolySlik ®, HP Smith). The casting solution was precisely deposited at 5 mils (pre-drying thickness) using a Gardner hand coating knife, and the solvents removed by drying the cast film in a drying oven at 65° C. for 20 min.

A backing was then laminated onto the dried anchor adhesive layer, the release liner removed, and an intermediate fiber layer applied (Reemay 2250). The resulting product was laminated to the contact adhesive layer using a hand pressure roller, applying pressure sufficient to force the anchor adhesive and contact adhesive to an interface within the structural layer, to form the final laminate. The laminate was then cut into 20 cm² rectangles with radiused corners, labeled, and sealed into foil pouches.

EXAMPLE 2

In vitro Flux Determination

Dermatomed dermis/epidermis (rejected for skin grafting) was obtained from a burn clinic. Samples were received refrigerated or frozen (stored in liquid nitrogen). All samples were frozen at −20° C. until used. The epidermis was removed from the dermis manually, after heating the sample in water at 60° C. for 2 minutes. The epidermis was floated on the water surface, then picked up and laminated between two sheets of cellulose acetate film. These preparations were used immediately, or were frozen for later use.

Test patches were prepared using the following formulations:

| | |
|---|---|
| A: | silicone contact adhesive: Dow Corning 2920; dexmedetomidine base: 1.8–2.2% (dry loading range = 0.5–3.0%); PGML: 8%; Polyester nonwoven layer: Reemay 2250 anchor layer: polyisobutylene mixture backing: 0.5 mil transparent polyester (3M #139) |
| B: | acrylic contact adhesive: Monsanto Gelva 737 & 788 mixture; dexmedetomidine base: 1.8–2.2% PGML: 8% Polyester nonwoven layer: Reemay 2250 anchor layer: polyisobutylene backing: 0.5 mil polyester (3M #139) |
| C: | acrylic contact adhesive: Gelva 737/788 mixture; dexmedetomidine base: 1.8–2.2% PGML: 12% Polyester nonwoven layer: Reemay 2250 anchor layer: polyisobutylene backing: 0.5 mil transparent polyester (3M #139 |
| D: | silicone contact adhesive: Dow Corning 2920; dexmedetomidine base: 1.8–2.2% PGML: 8% no intermediate layer anchor layer: polyisobutylene mixture backing: 0.5 mil polyester (3M #139) |
| E: | acrylic contact adhesive: Gelva 737/788 mixture; dexmedetomidine base: 1.8–2.2% PGML: 12% no intermediate layer anchor layer: polyisobutylene mixture backing: 0.5 mil polyester (3M #139) |

Skin circles were punched out of the epidermal preparation using an Arch punch, floated on water, and blotted dry on cellulose acetate film while checking for leaks. Patches prepared as set forth above were cut to the same dimensions, and laminated to the skin preparation (three for each formulation). Each laminate was then placed over the manually-sampled diffusion cell orifice of a Franz-type diffusion cell (horizontal skin plane), and was clamped in place. This cell has a receiver volume of 7.5 mL, a diffusion area of 0.689 cm$^2$, and was heated using an incubator at 32° C. The receiver fluid was phosphate-buffered isotonic saline, pH 5.0, containing 0.1% gentamycin. Sample volumes were 1.0 mL, drawn at 0.5, 1.0, 1.5, 2.0, 4.5, 17.0, 21.0, and 26.5 hours. Dexmedetomidine concentrations were determined by HPLC.

FIG. 3 depicts the cumulative amount of dexmedetomidine (in ug/cm$^2$) transmitted through the skin sample for each preparation (dotted squares=A, filled diamonds=B, open squares=C, open diamonds=D, and filled squares=E). The calculated fluxes are shown in Table I.

TABLE I

| Preparation | Average Flux | |
|---|---|---|
| | Flux (µg/cm2/hr) | Lag time (hours) |
| A | 3.9 | 1.0 |
| B | 3.5 | 1.7 |
| C | 4.4 | 0.9 |
| D | 3.4 | 1.1 |
| E | 4.6 | 1.9 |

The results demonstrate that the devices of the invention are capable of releasing therapeutically effective amounts of dexmedetomidine through human skin in vitro.

What is claimed is:

1. A method for sedating a patient, which method comprises:

transdermally administering dexmedetomidine to said patient through a predetermined area of intact skin for a time period and at an administration rate sufficient to effect sedation.

2. The method of claim 1, further comprising coadministering a skin permeation enhancer.

3. The method of claim 2, wherein said skin permeation enhancer comprises an ester of formula [CH$_3$(CH$_2$)$_m$COO]$_n$R, in which m is an integer in the range of 8 to 16, n is 1 or 2, and R is a lower alkyl (C$_1$-C$_3$) residue that is either unsubstituted or substituted with one or two hydroxyl groups.

4. The method of claim 2, wherein the dexmedetomidine is in base form.

5. The method of claim 1, wherein the administration rate is in the range of about 0.10 to about 200 ug/hr.

6. The method of claim 5, wherein the administration rate is in the range of about 15 to about 75 ug/hr.

7. The method of claim 5, wherein the area of intact skin is in the range of about 2.0 to about 90 cm$^2$.

8. The method of claim 6, wherein the area of intact skin is in the range of about 10 to about 30 cm$^2$.

9. The method of claim 1, wherein said time period is in the range of about 0.1 to about 96 hours.

10. The method of claim 1, wherein said time period is in the range of about 1 to about 48 hours.

11. The method of claim 1, wherein administration is continuous throughout said time period.

12. The method of claim 9, wherein administration is continuous throughout said time period.

13. The method of claim 10, wherein administration is continuous throughout said time period.

14. The method of claim 1, wherein the dexmedetomidine is in base form.

15. A system for administering dexmedetomidine transdermally through a predetermined area of intact skin, comprising:

(a) a backing layer which defines the upper surface of the device; and (b) a layer of a pressure-sensitive, pharmaceutically acceptable contact adhesive layer having an area substantially equal to said predetermined intact skin area, comprised of a material that is permeable to dexmedetomidine and which defines the basal surface of the device and contacts and adheres to the skin when the device is in use, wherein the dexmedetomidine is dispersed throughout said contact adhesive layer after equilibration in said device.

16. The system of claim 15, further comprising:

(c) an anchor adhesive layer positioned between the contact adhesive layer and the backing layer, and laminated thereto.

17. The system of claim 16, further comprising:

(d) a porous intermediate layer between said anchor adhesive layer and contact adhesive layers and which is permeable to the dexmedetomidine.

18. The system of claim 17, wherein said porous intermediate layer comprises a nonwoven fabric.

19. The system of claim 16, wherein said contact adhesive layer further comprises a skin permeation enhancer.

20. The system of claim 19, wherein the skin permeation enhancer comprises an ester of formula [CH$_3$(CH$_2$)$_m$COO]$_n$R, in which m is an integer in the range of 8 to 16, n is 1 or 2, and R is a lower alkyl (C$_1$-C$_3$) residue that is either unsubstituted or substituted with one or two hydroxyl groups.

21. The system of claim 15, wherein said area of contact adhesive is in the range of about 2.0 to about 90 cm$^2$, and the system is adapted to deliver dexmedetomidine at an administration rate in the range of about 0.10 to about 200 ug/hr.

22. The system of claim 21, wherein said area of contact adhesive is in the range of about 10 to about 30 cm$^2$, and the system is adapted to deliver dexmedetomidine at an administration rate in the range of about 15 to about 75 ug/hr.

23. The system of claim 16, wherein said anchor adhesive layer comprises polyisobutylene.

24. The system of claim 15, wherein said contact adhesive layer comprises an acrylate.

25. The system of claim 23, wherein said contact adhesive layer comprises an acrylate.

26. The system of claim 15, wherein the dexmedetomidine is in base form.

27. The system of claim 19, wherein the dexmedetomidine is in base form.

28. The system of claim 25, wherein the dexmedetomidine is in base form.

* * * * *